US012351496B2

(12) United States Patent
Liu et al.

(10) Patent No.: US 12,351,496 B2
(45) Date of Patent: Jul. 8, 2025

(54) MICROBIAL ASSISTED PHOSPHOROUS RECOVERY UNDER ANAEROBIC CONDITION

(71) Applicant: The Governors of the University of Alberta, Edmonton (CA)

(72) Inventors: Yang Liu, Edmonton (CA); Lei Zhang, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 352 days.

(21) Appl. No.: 17/837,308

(22) Filed: Jun. 10, 2022

(65) Prior Publication Data

US 2022/0396509 A1    Dec. 15, 2022

Related U.S. Application Data

(60) Provisional application No. 63/209,536, filed on Jun. 11, 2021.

(51) Int. Cl.
*C02F 3/12* (2023.01)
*C01B 25/32* (2006.01)
(Continued)

(52) U.S. Cl.
CPC .............. *C02F 3/28* (2013.01); *C01B 25/322* (2013.01); *C02F 3/1268* (2013.01); *C02F 3/341* (2013.01);
(Continued)

(58) Field of Classification Search
CPC ...... C01B 25/322; C02F 3/1268; C02F 3/341; C02F 2101/105; C02F 2101/16;
(Continued)

(56) References Cited

U.S. PATENT DOCUMENTS 5,114,586 A  *  5/1992  Humphrey  ............ C02F 3/1242
                                                              210/138
6,379,546 B1 *  4/2002  Braun  ...................... C05F 3/04
                                                              210/167.3
(Continued)

FOREIGN PATENT DOCUMENTS

CN      212246689 U  * 12/2020  ................ C02F 9/00
JP     2006187681 A  *  7/2006
(Continued)

OTHER PUBLICATIONS

English Translation of Publication CN 212246689. (Year: 2020).*
(Continued)

*Primary Examiner* — Joseph W Drodge
(74) *Attorney, Agent, or Firm* — MaxGoLaw PLLC

(57) ABSTRACT

A system and method for treatment of wastewater, in which the system includes a blackwater reactor configured to receive a stream of blackwater influent, to contain the blackwater therein during treatment of the blackwater, to facilitate recovery of methane and nutrient precipitates therefrom, and to output partially treated blackwater, and a greywater reactor configured to receive a stream of greywater influent and the partially treated blackwater output from the blackwater reactor, to contain the greywater and the partially treated blackwater therein during greywater treatment, and to output greywater treatment discharge. The process includes inputting a stream of blackwater into the blackwater reactor; treating the blackwater in the blackwater reactor with an anaerobic digestion process; controlling a pH level of the blackwater within the blackwater reactor; recovering nutrient precipitates from the blackwater reactor, optionally independent of chemical additives; and recovering methane from the blackwater reactor.

11 Claims, 14 Drawing Sheets

(51) Int. Cl.
| | |
|---|---|
| C02F 3/28 | (2023.01) |
| C02F 3/34 | (2023.01) |
| C05B 1/04 | (2006.01) |
| C07C 7/00 | (2006.01) |
| C02F 101/10 | (2006.01) |
| C02F 101/16 | (2006.01) |
| C02F 101/30 | (2006.01) |
| C02F 103/00 | (2006.01) |

(52) U.S. Cl.
CPC ................ C05B 1/04 (2013.01); C07C 7/00 (2013.01); C02F 2101/105 (2013.01); C02F 2101/16 (2013.01); C02F 2101/301 (2013.01); C02F 2103/002 (2013.01); C02F 2103/005 (2013.01); C02F 2209/06 (2013.01); C02F 2301/106 (2013.01); C02F 2303/12 (2013.01)

(58) Field of Classification Search
CPC .......... C02F 2101/301; C02F 2103/002; C02F 2103/005; C02F 2209/06; C02F 2301/106; C02F 2303/12; C02F 1/28; C02F 2209/02; C02F 2209/07; C02F 2209/08; C02F 3/28–2893; C02F 11/04; C02F 3/006; C05B 1/04; C07C 7/00; Y02E 50/30; Y02W 10/10
See application file for complete search history.

(56) References Cited

U.S. PATENT DOCUMENTS

| | | | | |
|---|---|---|---|---|
| 2003/0070986 A1* | 4/2003 | Braun | ....................... | C02F 9/00 210/620 |
| 2007/0068879 A1* | 3/2007 | Markle | ..................... | C02F 9/00 210/202 |
| 2011/0186489 A1* | 8/2011 | Kain | ......................... | C02F 9/00 210/150 |
| 2012/0217201 A1* | 8/2012 | Ngo | ...................... | C02F 3/1268 435/243 |
| 2014/0151294 A1* | 6/2014 | Prior | ........................ | C02F 9/00 210/151 |
| 2014/0263045 A1* | 9/2014 | Mazumdar | ................ | C02F 3/02 210/150 |
| 2021/0024394 A1* | 1/2021 | Warner | ..................... | C02F 9/00 |
| 2021/0395125 A1* | 12/2021 | Yeh | .......................... | C02F 9/00 |

FOREIGN PATENT DOCUMENTS

| | | | |
|---|---|---|---|
| RU | 2513691 C2 * | 4/2014 | |
| WO | WO-2009101528 A1 * | 8/2009 | ............ C02F 1/4608 |

OTHER PUBLICATIONS

English translation of Publication JP 2006187681A, published Jul. 20, 2006. (Year: 2006).*
English translation of publication RU 2513691C2, published Apr. 20, 2014. (Year: 2014).*
English translation of publication WO 2009101528A1, published Aug. 20, 2009. (Year: 2009).*
Chen Y., et al. High-purity propionate production from glycerol in mixed culture fermentation. Bioresour Technol 2016; 219:659-667.
Cheng Z., et al. Enhancement of surfactant biodegradation with an anaerobic membrane bioreactor by introducing microaeration. Chemosphere 2018; 208:343-351.
Cunha J. R., et al. Calcium addition to increase the production of phosphate granules in anaerobic treatment of black water. Water Research 2018; 130:333-342.
Cunha J. R., et al. The Effect of Bioinduced Increased pH on the Enrichment of Calcium Phosphate in Granules during Anaerobic Treatment of Black Water. Environ. Sci. Technol. 2018; 52:13144-13154.
Daneshgar S., et al. Impact of pH and ionic molar ratios on phosphorous forms precipitation and recovery from different wastewater sludges. Resources. 2018; 7(4):71.
De Graaff M. S., et al. Anaerobic Treatment of Concentrated Black Water in a UASB Reactor at a Short HRT. Water. 2010; 2(1):101-119.
De La Rubia M. A., et al. Thermophilic anaerobic digestion of sewage sludge: Focus on the influence of the start-up. A review. Crit Rev Biotechnol. 2013; 33(4):448-60.
Elmitwalli T. A., et al. Anaerobic biodegradability and treatment of grey water in upflow anaerobic sludge blanket (UASB) reactor. Water Res 2007; 41(6):1379-1387.
Faria C. V., et al. Strategies of anaerobic sludge granulation in an EGSB reactor. Journal of Environmental Management 2019; 244:69-76.
Florentino A. P., et al. Overcoming ammonia inhibition in anaerobic blackwater treatment with granular activated carbon: the role of electroactive microorganisms. Environmental Science: Water Research & Technology 2019; 5 (2):383-396.
Fukuzaki S., et al. High rate performance and characterization of granular methanogenic sludges in upflow anaerobic sludge blanket reactors fed with various defined substrates. J Ferment Bioeng 1995; 79(4):354-359.
Gao M., et al. Microbial community dynamics in anaerobic digesters treating conventional and vacuum toilet flushed blackwater. Water Res 2019; 160:249-258.
Gao M., et al. Biomethane recovery from source-diverted household blackwater: Impacts from feed sulfate. Process Safety and Environmental Protection 2020;136:28-38.
Gao M., et al. Enhancing biomethane recovery from source-diverted blackwater through hydrogenotrophic methanogenesis dominant pathway. Chem. Eng. J. 2019; 378:122258.
Gao M., et al. High-loading food waste and blackwater anaerobic co-digestion: Maximizing bioenergy recovery. Chem. Eng. J. 2020; 394:124911.
Jang H. M., et al. Reactor performance and methanogenic archaea species in thermophilic anaerobic co-digestion of waste activated sludge mixed with food wastewater. Chem Eng J 2015;276:20-28.
Moges M. E., et al. Sludge blanket anaerobic baffled reactor for source separated blackwater treatment. Water Sci Technol 2018; 78(6):1249-1259.
Rose C., et al. The characterization of feces and urine: A review of the literature to inform advanced treatment technology. Critical Reviews in Environmental Science and Technology 2015; 45:1827-1879.
Teo K.C., et al. Molecular mechanism of granulation. II: Proton translocating activity. Journal of Environmental Engineering 2000; 126(5):411-418.
Tervahauta T., et al. Calcium phosphate granulation in anaerobic treatment of black water: A new approach to phosphorus recovery. Water Res 2014; 48(1):632-642.
Wendland C., et al. Anaerobic digestion of blackwater from vacuum toilets and kitchen refuse in a continuous stirred tank reactor (CSTR). Water Sci. Technol; 2007; 55(7):187-194.
Westerholm M., et al. Biogas production through syntrophic acetate oxidation and deliberate operating strategies for improved digester performance. Applied Energy 2016;179:124-135.
Yee R.A., et al. Nutrient recovery from source diverted blackwater: Optimization for enhanced phosphorus recovery and reduced co-precipitation. Journal of Cleaner Production 2019; 235:417-425.
Yee R.A., et al. Evaluating Microbial and Chemical Hazards in Commercial Struvite Recovered from Wastewater. Environ. Sci. Technol. 2019; 53(9):5378-5386.
Yoochatchaval W., et al. Characteristics of granular sludge in an EGSB reactor for treating low strength wastewater. International Journal of Environmental Research 2008; 2(4):319-328.
Zhang L., et al. Hydrolysis rate constants at 10-25 ° C. can be more than doubled by a short anaerobic pre-hydrolysis at 35 ° C. Water Res 2016; 104:283-291.
Zhang L., et al. Blackwater Biomethane Recovery using a Thermophilic Upflow Anaerobic Sludge Blanket Reactor: Impacts of Effluent Recirculation on Reactor Performance. Journal of Environmental Management 2020; 274:111157.

(56) References Cited

OTHER PUBLICATIONS

Zhang L., et al. Co-digestion of blackwater with kitchen organic waste: Effects of mixing ratios and insights into microbial community. Journal of Cleaner Production 2019; 236:117703.

Zhang Q., et al. Mesophiles outperform thermophiles in the anaerobic digestion of blackwater with kitchen residuals: insights into process limitations. Waste Mana (Oxford) 2020; 105:279-288.

* cited by examiner

Table 1
Summary of COD removal, methane production rate, VFA and $NH_4^+$-N in phases I-V (unit: g/L, standard deviation is in brackets)

| Phases | Influent | | | | | Effluent | | | | | $COD_{total}$ removal efficiency (%) | Methane yield (%) |
|---|---|---|---|---|---|---|---|---|---|---|---|---|
| | $COD_{total}$ | $COD_{suspended}$ | $COD_{soluble}$ | VFA | $NH_4^+$-N | $COD_{total}$ | $COD_{suspended}$ | $COD_{soluble}$ | VFA | $NH_4^+$-N | | |
| Phase I | 18.8 | 14.9 | 4.0 | 0.9 | 1.07 | 4.3 | 1.6 | 2.6 | 0.7 | 1.27 | 77.5 | 44.4 |
| (OLR 0.9) | (3.2) | (2.6) | (1.2) | (0.3) | (0.10) | (1.2) | (0.7) | (0.8) | (0.3) | (0.09) | (4.4) | (3.8) |
| Phase II | 33.5 | 29.1 | 4.4 | 0.8 | 1.21 | 5.0 | 2.6 | 2.3 | 0.3 | 1.45 | 81.9 | 50.5 |
| (OLR 1.6) | (4.3) | (5.3) | (1.2) | (0.5) | (0.15) | (1.4) | (1.3) | (0.6) | (0.3) | (0.17) | (5.5) | (6.3) |
| Phase III | 33.2 | 27.1 | 6.1 | 1.3 | 1.28 | 5.4 | 3.6 | 1.7 | 0.1 | 1.52 | 83.6 | 60.8 |
| (OLR 3.4) | (2.9) | (3.3) | (0.9) | (0.3) | (0.12) | (0.3) | (0.4) | (0.3) | (0) | (0.11) | (2.1) | (1.8) |
| Phase IV | 27.7 | 22.7 | 5.0 | 1.0 | 1.24 | 5.5 | 4.2 | 1.3 | 0.2 | 1.38 | 79.8 | 57.8 |
| (OLR 5.9) | (3.7) | (3.1) | (1.0) | (0.9) | (0.18) | (0.6) | (0.7) | (0.2) | (0.1) | (0.14) | (3.7) | (6.8) |
| Phase V | 32.0 | 25.7 | 6.4 | 1.4 | 1.32 | 5.2 | 3.8 | 1.5 | 0.2 | 1.49 | 81.9 | 55.9 |
| (OLR 12.4) | (1.7) | (3.7) | (1.8) | (0.5) | (0.12) | (0.9) | (0.5) | (0.3) | (0.1) | (0.10) | (1.9) | (6.2) |

FIG. 13

MICROBIAL ASSISTED PHOSPHOROUS RECOVERY UNDER ANAEROBIC CONDITION

RELATED APPLICATIONS

This application claims priority benefit of U.S. Provisional Application Ser. No. 63/209,536 filed on Jun. 11, 2021, the contents of which are hereby incorporated by reference.

FIELD OF INVENTION

The present invention generally relates to methods of wastewater treatment, and more particularly to methods of wastewater treatment using anaerobic biological conditions, which are controlled to provide optimized nutrient recovery and methane production.

BACKGROUND

Phosphorous is an essential plant nutrient which is used in agriculture. Phosphorus consumption increases faster and faster due to population growth and industry development. Phosphorous is mined, but the resource is limited, with recent reports predicting that the natural deposits of phosphorus will be exhausted in only 30 to 100 years. Most of the mined phosphorous is discharged or lost to the environment during food production and consumption. Significant discharge of phosphorous in the environment has led to eutrophication of streams, lakes, or estuaries having detrimental impact on agriculture and aquatic life.

Efficacy of energy, nutrient, and water recovery from municipal wastewater can be maximized by implementing decentralized source-diverted blackwater-only localized sewers (wastewater from toilets/urinals and kitchen food waste grinders) diverted from local greywater (all other household water) collection/treatment systems as shown in FIG. 1. Source-diverted blackwater, containing most of the organic energy and over 90% of the nutrients in domestic wastewater, can be collected via a local sealed vacuum conveyance system and treated for energy (as biomethane) and nutrient (as fertilizer) recovery; the remaining household water (i.e. greywater), representing (some 70% of conventional sewage volume), can be then treated to provide fit-for-purpose local water reuse (potentially combined with stormwater). This approach can be incorporated for greenfield developments and communities where sewage source-diversion and greywater treatment are already in place.

Currently, source-diverted, resource-recovery based blackwater and greywater systems have only been demonstrated at small community scale in a few countries around the world. The European blackwater treatment technology utilizes a three-reactor configuration, as shown in FIG. 2, an upflow anaerobic sludge blanket (UASB) and anaerobic digester (AD) for biogas recovery, and oxygen limited autotrophic nitrification denitrification (OLAND) reactor for nitrogen reduction, and a nutrient recovery reactor that produces solid struvite ($MgNH_4PO_4$) fertilizer. The greywater treatment technology utilizes a conventional two-stage adsorption/bio-oxidation process for organics reductions. A major challenge with European blackwater treatment systems is that they require a large footprint (i.e. large reactors), hence is only economically viable for high density communities (1000-2000 residents) due to a) low blackwater methanongenesis rates in UASB largely due to free ammonia inhibition and low methane yields, b) low specific anoxic ammonium oxidation activities in OLAND, dues to phosphorous inhibition, c) high operating costs with the struvite reactor, due to extensive pH adjustment (from 7 to 8.5) and $MgCl_2$ addition required for phosphorous (in the form of struvite) recovery; and d) low greywater organics removal efficiency due to high recalcitrant surfactants content and low nutrient availability (i.e. high C:N ratio) to support complete aerobic degradation.

It is possible to recover phosphorous from various waste streams, particularly sewage and agricultural wastewater, and food processing streams. Anaerobic wastewater treatment is well established in the industry. Water treatment of toilet water is well defined in large scale municipal treatment plants, smaller scale household septic tanks, as well as some established processed for treatment of toilet water from community sized systems. Use of vacuum toilet water, which has less dilution and high COD (high levels of organic solids) is emerging as a challenge with established processes.

Phosphorus recovery occurs within wastewater treatment facilities or in downstream anaerobic agricultural or municipal wastewater stabilization processes. These processes are well established in the art. Anaerobic digestion causes breakdown of solids, generation of methane, nutrients (phosphorous and ammonia) and other ions (calcium, magnesium). However, conventional processes are multi-stage with an initial anaerobic digestor, followed by various anoxic (limited oxygen, using nitrate as electron acceptor), aerobic or physiochemical treatments as post treatment of anaerobic digestors to remove nutrients and other contaminants. Anaerobic domestic wastewater treatment has advantages of energy recovery in terms of methane, less waste sludge production and lower operational cost compared with aerobic wastewater treatment. Typical microbial processes involve hydrolysis, acidification, acidogenesis and methanogenesis. As described in Environ Sci. Water Res. Technolo, 2019 5, 383-396, "conventionally, in anaerobic degradation, complex organic matter is hydrolyzed to monomeric organic materials that are afterward fermented by acidogenic bacteria generating acetate and small organic molecules such as lactate, succinate, and fatty acids; syntrophic bacteria convert such molecules to acetate, hydrogen and formate. Methanogenic archaea, in turn, convert acetate into methane and carbon dioxide, or utilize the electrons from hydrogen and formate to reduce carbon dioxide to methane." Additionally, chemicals must be added to help control process steps, such as to alter the pH to promote phosphorous recovery, given that it is well established that increasing pH to 8-10.5 promotes phosphorous precipitation. For chemical precipitation of phosphate from wastewater, lime and the salts of iron and aluminum have been the chemicals of choice for process development.

Thus, there exists a need for a phosphorus recovery process from domestic wastewater that does not require any chemical addition, that optimizes nutrient recovery, and that reduces the footprint of the wastewater treatment plant and operational cost compared with traditional domestic wastewater treatment.

SUMMARY

The present disclosure provides a system for treatment of wastewater that includes a blackwater reactor and a greywater reactor and a method for using the system. The blackwater reactor is configured to receive a stream of blackwater influent, to contain the blackwater therein during treatment of the blackwater, to facilitate recovery of methane and nutrient precipitates therefrom, and to output partially treated blackwater. The greywater reactor is configured to receive a stream of greywater influent and the partially treated blackwater output from the blackwater reactor, to contain the greywater and the partially treated blackwater therein during greywater treatment, and to output greywater treatment discharge.

The present disclosure additionally includes a process for treating wastewater using the inventive system. The process includes inputting a stream of blackwater into the blackwater reactor; treating the blackwater in the blackwater reactor with an anaerobic digestion process, optionally independent of mixing; controlling a pH level of the blackwater within the blackwater reactor; recovering nutrient precipitates from the blackwater reactor, optionally independent of chemical additives; and recovering methane from the blackwater reactor.

The present disclosure additionally provides phosphorus rich precipitate produced by the process for treating wastewater using the inventive system.

BRIEF DESCRIPTION OF THE DRAWINGS

The present invention is further detailed with respect to the following drawings that are intended to show certain aspects of the present of invention, but should not be construed as limit on the practice of the invention, wherein:

FIG. 13 is a table showing a summary of COD removal, methane production rate, VFA and $NH_4^+$—N in phases I-V.

DETAILED DESCRIPTION

Figure 1:
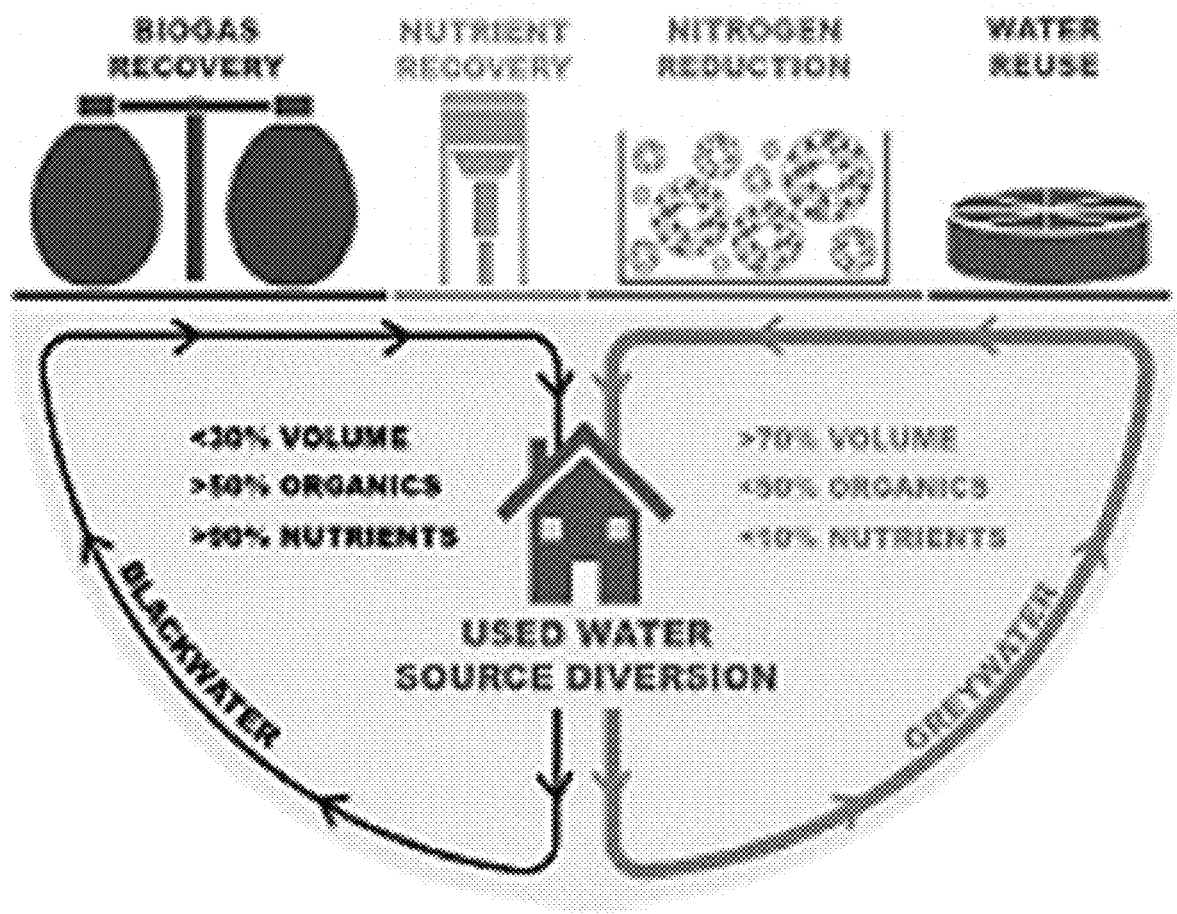
FIG. 1 shows a schematic of existing decentralized source-diverted blackwater and greywater treatment system.

The present invention has utility as a method of wastewater treatment using anaerobic biological conditions, which are controlled to provide optimized nutrient recovery and methane production. The inventive method does not require any chemical addition, that optimizes nutrient recovery, and that reduces the footprint of the wastewater treatment plant and operational cost compared with traditional domestic wastewater treatment.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

The present invention provides a method to recover phosphorus in anaerobic domestic wastewater treatment through manipulating microbial pathway. The localized chemical condition can be biologically adjusted to simultaneously achieve energy in terms of methane and nutrient (phosphorus) recovery in a single reactor.

Methane production in anaerobic digestion is carried out with bacteria and archaea through four steps: hydrolysis, acidogenesis, acetogenesis and methanogenesis. Given wastewater matrix, such as organic materials (protein, lipid, polysaccharide), cation ($NH^{4+}$, $Na^+$, $Mg^{2+}$, $Ca^{2+}$, $Al^{3+}$) and anion ($Cl^-$, $HCO_3^-$, $SO_4^{2-}$, $PO_4^{3-}$), localized environmental conditions around anaerobic microbes, such as alkalinity, pH and mixing condition varies under the different operational parameters. According to embodiments, the temperature of the anaerobic reactor is applied between 35-55° C., the anaerobic reactor type, expanded granular sludge bed reactor (EGSB) and up-flow anaerobic sludge bed reactor (UASB)) is investigated at a hydraulic retention time (HRT) of 2-4 ds and organic loading rate (OLR) of 1-6 kg COD/(m³d)). Conductive materials, such as granular activated carbon and graphite are chosen to facilitate hydrogenotrophic methanogenesis. As a result, a feasible condition closed to the enriched anaerobic microbes is established to precipitate phosphorus from the domestic wastewater, which is $Ca_{10}(PO_4)_6(OH)_2$ (HAP), $Ca_3(PO_4)_2$ (TCP), $Ca_3(PO_4)_2 \cdot xH_2O$ (ACP), $Ca_s(HPO_4)_2(PO_4)_4 \cdot 5H_2O$ (OCP), $CaHPO_4$ (DCP), and $CaHPO_4 \cdot 2H_2O$ (DCPD). The anaerobic granular sludge enriched phosphorus is produced in the CaP form. Advantageously, the present invention does not require any chemical addition, integrates methane production and phosphorus recovery in one reactor, saves footprint of the wastewater treatment plant and operational cost compared with traditional domestic wastewater treatment.

The present invention provides a method of phosphorous recovery using anaerobic biological conditions, which are controlled to provide optimized nutrient recovery and methane production. The process is suitable for implementation on various sewage and wastewater streams as feed to the process. According to embodiments, the inventive method is applied to blackwater from vacuum toilets. According to embodiments, an upflow anaerobic sludge blanket (UASB) reactor is used. The UASB reactor is inoculated with a 1:1 inoculum which can be obtained from any normal anaerobic sludge digestor so as to increase the concentration of anaerobic bacteria in the toilet water feed. The present invention provides the unique benefit that the optimal process design of the UASB reactor allows for achieving simultaneous energy and phosphorous recovery, as well as nitrogen recovery. The optimal design produces a method of reducing current source-diverted blackwater/greywater treatment processes from five key unit operations to three; this leads to gains in energy efficiency, recovery of nutrients, and simpler integrated systems for different scalability to meet community needs. Additional features of embodiments of the present invention include:

- Requiring only one anaerobic biological reactor step to degrade organic solids (waste material), produce biogas (energy resource) and recover phosphorous (nutrient recycle);
- Providing microbes in the UASB reactor develop localized pH and water chemistry variations through protein and urea hydrolysis of the organic waste, which causes localized pH elevation able to precipitate the phosphorous, without the addition of chemicals;
- Controlling feeding such that pH increases rapidly;
- Producing methane gas in the UASB to help carry the flow upwards, which can be recovered by usual gas capture ports;
- Not requiring mixing apparatus in the bioreactor (other methods promote mixing in a CSTR to increase biogas yield), given that in the present invention, mixing is detrimental to phosphorous recovery in that it disrupts the localized environments around cells which result in the phosphorous precipitation, yet even without the mixing apparatus the present invention is not detrimental to biogas recovery as similar or better yields of biogas are attainable in the process using the UASB;
- Not relying on chemical treatments to provide conditions of precipitation (which is typical of most treatment processed) but relies on the $Ca^{2+}$ level in the organic waste stream to provide the $Ca^{2+}$ to form the phosphorous precipitate;
- Creating easily recoverable granules which contain the accumulated phosphorous for recovery, these granules being easily collectable from the blanket sludge layer;
- Optimizing temperature in mesophilic to thermophilic range (35-55° C.) for more efficient operation;
- Loading with higher organic load (high carbon content) allowing bugs to grow and resulting in a high phosphorus content in the feed.

Figure 2:
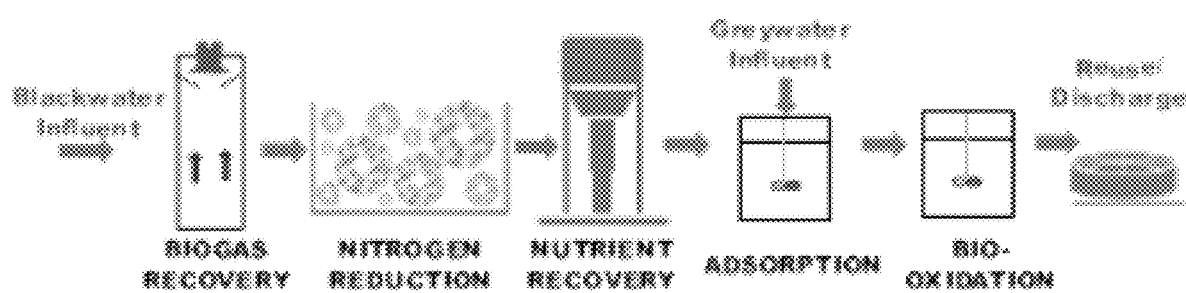
FIG. 2 shows a schematic of existing European blackwater treatment technology.
Figure 3:
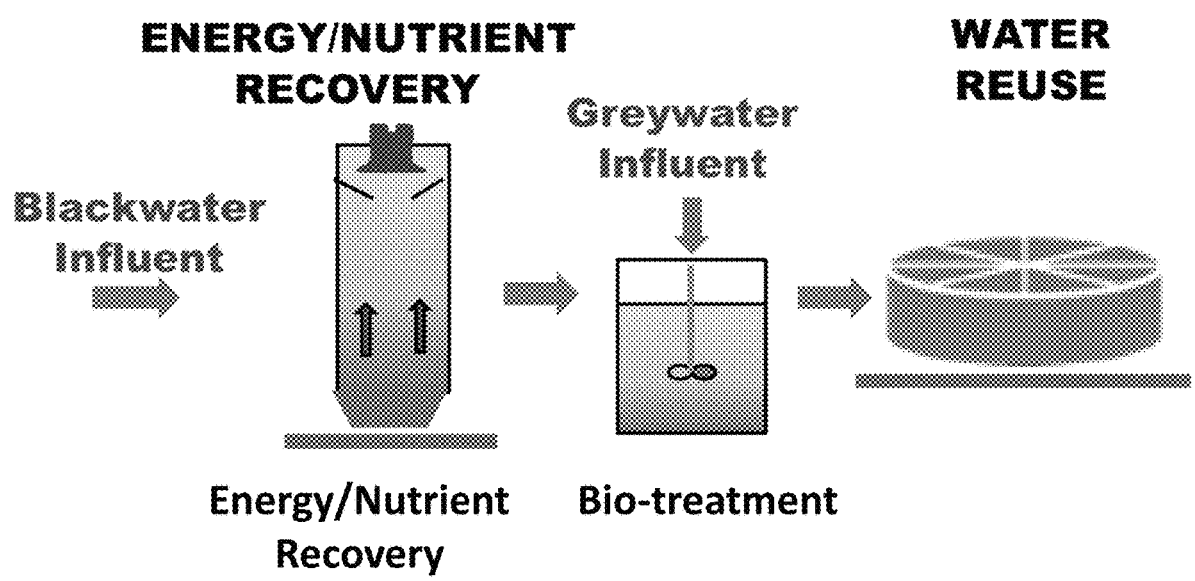
FIG. 3 shows a schematic of an integrated black/Greywater treatment system according to embodiments of the present invention.

The present invention provides an integrated blackwater energy and nutrient recovery system, as shown in FIG. 3. The inventive system improves upon existing systems such as the European system of FIG. 2 by enhancing methane production through eliminating free ammonic inhibition and enhancing the chemical costs required for P recovery.

Materials and Methods

Thermophilic UASB Reactor Set-Up

A 2 L laboratory-scale UASB reactor is used to treat blackwater under thermophilic condition (52° C.) as described by Zhang et al. (2020a), using a temperature-controlled water bath. Thermophilic anaerobic sludge inoculum is collected from an anaerobic thermophilic reactor for anaerobic co-digestion of blackwater and organic kitchen waste (Zhang et al. 2020b) and had a sludge volatile suspended solids (VSS) concentration of 13.1 g/L. Blackwater is collected from the University of Alberta (Edmonton, Canada) campus, as described by Gao et al. (2019a). Blackwater and the thermophilic sludge are mixed at a 1:1 ratio as the seed for reactor start-up. Polystyrene foam is used to cover the heating blanket to maintain the reactor temperature. The experiment is divided into five phases (i.e. I-V) based on the OLR applied, being 0.9, 1.7, 3.4, and 5.4 and 12.9 kg COD/(m³d), respectively. The HRT during the reactor startup is 20 d (for Phases I and II), which is then reduced to 10 days (Phase III), 5 days (Phase IV) and 2.5 days (Phase V) for the rest of the experiment. Each phase is operated until chemical oxygen demand (COD) removal and methane yield became stable (for at least 20 ds).

Influent, Effluent Water Index and Biogas Composition Analysis

Influent and effluent COD concentration, phosphate phosphorus concentration and pH are determined according to the standard methods of American Public Health Association (APHA) (APHA 2012). Ammonia nitrogen of the influent and effluent is measured using Nessler ammonia Quantification Reagent Kit. Calcium concentration of the influent and effluent is measured using Hach 2319900 hardness reagent set (calmagite colorimetric).

Volatile fatty acids (VFAs), specifically acetate, propionate, and butyrate, are analyzed by a Dionex ICS-2100 ion chromatograph equipped with an IonPac AS18 column and 4.5 mM carbonate/1.4 mM bicarbonate eluent at a flow rate of 0.25 mL/min (Dionex, Sunnyvale, CA). The volume of biogas is collected in a Tedlar bag (VWR International, America), and is measured using a syringe every 1-2 days. The composition of biogas is quantified using a gas chromatography (GC) (7890B Agilent Technologies, Santa Clara USA; Column: Molsieve 5A 2.44 m 2 mm and Hayesep N 1.83 m 2 mm; carrier gas: argon; temperature: column of 100° C., injector of 150° C., detector of 200° C.).

Chemical Modeling for Saturation Index Calculation

The saturation indexes (SI) of $Ca_x(PO_4)_y$ (TCP, ACP and HAP) and struvite ($MgNH_4PO_4 \cdot 6H_2O$) are calculated using the software Visual Minteq 3.1 (KTH, Sweden) for equilibria simulation in blackwater. The SI of the determined compound is calculated according to Equation [1].

$$SI = \log\frac{IAP}{K_{sp}} \quad \text{Equation 1}$$

IAP is the ion activity product of the compound and Ksp is the solubility product constant. A SI>0 is considered supersaturated; SI<0, undersaturation, and SI=0, in apparent equilibrium. The numeric values of the nutrient precipitates during anaerobic digestion of blackwater are input for each situation to calculate SI.

Characteristics of Sludge Samples

Total suspended solids (TSS) and volatile suspended solids (VSS) of the sludge in the thermophilic UASB reactor are measured according to the standard methods of American Public Health Association (APHA) (APHA, 2012). Specific methanogenic activity (SMA) test is performed, following methods reported by Zhang et al. (2020a). Briefly, the UASB sludge is collected and mixed with substrates (acetate, propionate, butyrate, and $H_2$ and $CO_2$ at a ratio of 80:20) into 157 mL serum bottles and is performed in triplicate. The initial substrate concentration is 1.0 g-COD/L under all conditions. Samples are flushed with nitrogen to provide an anaerobic condition and placed in a shaker (New Brunswick™ Innova® 44, Eppendorf, Canada) at 55° C. with a mixing speed of 120 rpm. The pressure and gas composition of the bottle headspace are measured twice per day. Sludge samples are collected at the end of each phase.

The particle size distribution is conducted by employing a high-resolution camera (1024×768) (EOS 60D, Canon). Briefly, sludge samples are transferred from UASB to Petri dishes for photography, where the average size of the granular sludge particles is estimated from 50 randomly-selected particles in each photo. To evaluate the chemical composition of the granular sludge, sludge samples are dried at 105° C., grinded and acidified before metal elements characterization using an inductively coupled plasma mass spectroscopy (ICP-MS) (Perkin Elmer Elan 6000, Canada) method. The surface functional groups of the sludge are examined using X-ray diffraction (XRD) (Rigaku Ultimate IV, Japan) technique. The structure morphology of the UASB sludge is visualized by scanning electron microscope (SEM) (Zeiss Sigma 300 VP-PESEM, USA) and the element distribution on sludge surface is determined by energy dispersive X-ray spectroscopy (EDX) (Bruker EDX system, USA).

Calculation of P Mass Balance

The phosphorus mass balance of the blackwater treatment using the thermophilic UASB reactor is calculated according to Equation [2]:

$$P_{influent} = P_{CaP} + P_{cell\ uptake} + P_{effluent} \quad \text{Equation 2}$$

Where P influent and P effluent are average P amount entering and leaving the UASB reactor (g/d); PCaP (g/d) represents P precipitated as CaP; and Pcell uptake (g/d) refers to P incorporated into biomass (2% of dry biomass). The measurements are based on ICP-MS measurements described above.

DNA Extraction and Metagenomics Analysis

Genomic DNA is extracted according to the manufacturer's manual using the PowerSoil Kit (QIAGEN, Hilden, Germany). The DNA quantity and purity are determined using a NanoDrop One device (Thermo Fisher, Walthan, MA, USA). The DNA is analyzed using shot-gun sequencing on an Illumina Hiseq 2500 platform (Majorbio, Shanghai, China). The unassembled sequence reads are quality filtered using fastp (Chen et al. 2018) to retain high-quality reads (length>50 bp, Q>20). The clean reads are assembled using Megahit (https://github.com/voutcn/megahit) with minimum length of 300 bp, which are used to predict Open Reading Frame (ORF) using MetaGene (http://metagene.cb.k.u-tokyo.ac.jp/). Nonredundant representative sequences are obtained using CD-HIT (Cluster Database at High Identity with Tolerance, http://www.bioinformatics.org/cd-hit/) and annotated using BLAST (http://blast.ncbi.nlm.nih.gov) and databases (SwissProt, Protein Information Resource, Protein Research Foundation, Protein Data Bank, GenBank and RefSeq) with e-value cutoff of 1e-5. Functional genes are annotated using KEGG database (Kyoto Encyclopedia of Genes and Genomes, http://www.genome.jp/kegg/) to get K numbers and enzyme commission (EC) numbers.

Results

Blackwater COD Reduction and Methane Production

Figures 4A, 4B:
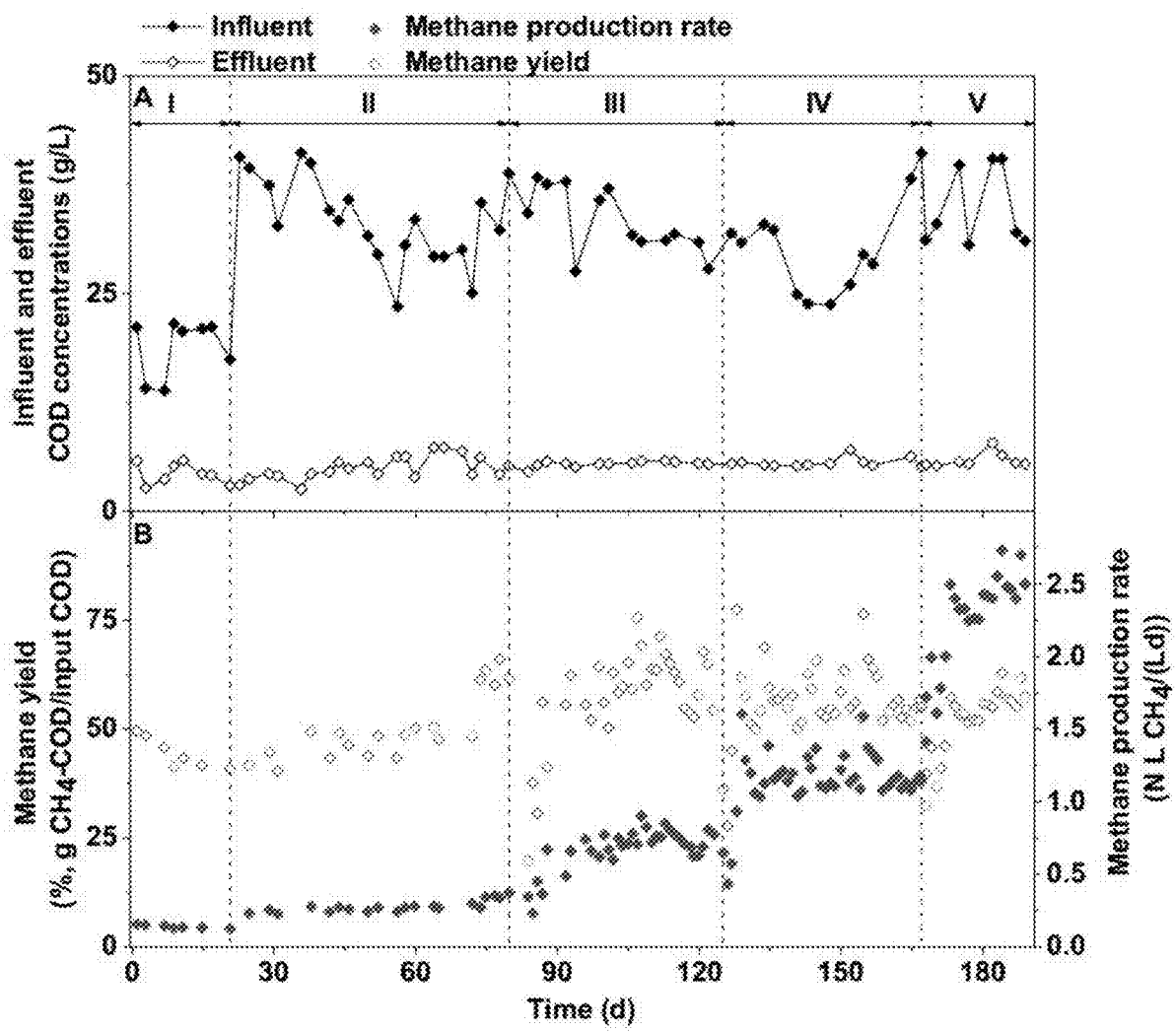
FIG. 4A is a graph showing profiles of COD concentrations in influent and effluent of UASB over the reactor operation time where OLR in Phase I-V are 0.9, 1.6, 3.4, 5.9 and 12.4 kg COD/(m$^3$d), respectively.
FIG. 4B is a graph showing methane yield and methane production rate over the reactor operation time where OLR in Phase I-V are 0.9, 1.6, 3.4, 5.9 and 12.4 kg COD/(m$^3$d), respectively.

Thermophilic UASB blackwater treatment achieved 77.5±4.4%-83.6±2.1% COD removal for all five phases examined (OLR from 0.9-12.4 kg COD/($m^3$d), as shown in Table 1 provided in FIG. 13. The influent COD concentrations varied from 27.7±3.7 g/L to 33.5±4.3 g/L over the operation period, as shown in FIG. 4A, excluding the start-up phase and contained high suspended COD concentration, ranging from 22.7±3.1 g/L to 29.1±5.3 g/L (Table 1, shown as FIG. 13).

The methane yield increased from 44.4±3.8% at the start-up phase (Phase I, OLR=0.9 kg COD/($m^3$d)) to 60.8±1.8% in Phase III (OLR=3.4 kg COD/($m^3$d)), and remained similar at 57.8±6.8% in Phase IV (OLR=5.9 kg COD/($m^3$d)) and 55.9±6.2% for Phase V (OLR=12.4 kg COD/($m^3$d)). This OLR is three-fold the previous highest OLR reported for anaerobic digestion of blackwater, at 4.1 kg COD/($m^3$d) (Gao et al. 2019b). Importantly, the methane production rate increased from 0.1 to 2.4±0.1 NL $CH_4$/(L d) from Phase I to V, as shown in FIG. 4B.

Throughout all phases the effluent VFA concentrations are low (0.1-0.3 g COD/L), and as expected the ammonia nitrogen concentration rose significantly from an average of 1.22±0.10 g $NH_4$—N/L in influent to 1.42±0.10 g $NH_4$—N/L in reactor effluent (Table 1); probably due to the ammonification of blackwater protein.

Blackwater Phosphate Recovery

Figures 5A, 5B:
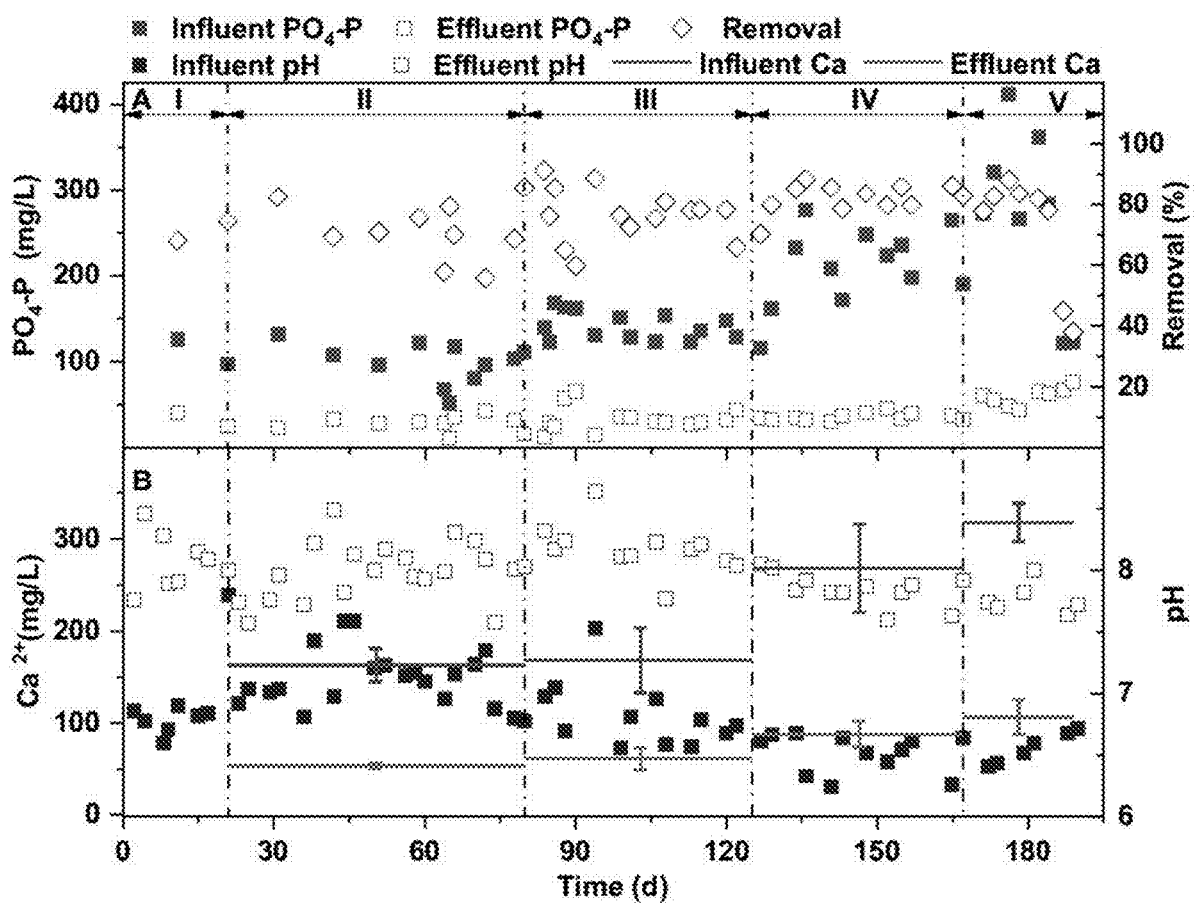
FIG. 5A is a graph showing profiles of $PO_4$—P in the UASB reactor influent and effluent over the reactor operation time where error bars represent standard deviation of at least five samples in each phase.
FIG. 5B is a graph showing profiles of $Ca^{2+}$ and pH in the UASB reactor influent and effluent over the reactor operation time where error bars represent standard deviation of at least five samples in each phase.

What is at the most exciting is that, without chemical addition, $PO_4^{3-}$—P removal (average of 77.7±8.5%) is achieved throughout the entire operation period of 190 days, as shown in FIG. 5A. Although the average influent $PO_4^{3-}$—P concentration in these phases varied (98.7-210.6 mg/L), effluent $PO_4^{3-}$—P concentration remained relatively stable (33.2±10.3 mg/L from Phase I to IV). The effluent $PO_4^{3-}$—P concentration in Phase V rose to 60.0±10.4 mg/L, possibly due to the high influent $PO_4^{3-}$—P concentration of 319.5±57.8 mg/L in the collected blackwater.

Conswastent with precipitation of calcium phosphates, the total calcium concentration present in the blackwater also decreased after anaerobic treatment, at a molar ratio of reduction (Ca:P) of 1.0±0.3, as shown in FIG. 5B. The average influent total Ca concentration varied between 168.0-268.2 mg/L, which clearly decreased to 61.7-83.0 mg/L in the effluent in the studied phases. In comparison, Cunha et al. (2018a) operated an UASB reactor treating blackwater by adding Ca2+ to the reactor influent (144-460 Ca2+mg/L), and the molar ratio of reduction (Ca:P) ranged between 1.19-3.01±0.21, indicating a lower Ca concentration per mole of P recovery is necessary in the present study. Most importantly, no external calcium source is required to achieve very effective phosphorus recovery.

Given the role of increasing pH to facilitate phosphorus recovery (precipitation), another feature of the thermophilic blackwater treatment is its pH increase, presumably facilitated by protein/urea hydrolysis as shown in Equations [3]-[6]. Over Phases I-V, influent pH is 6.9±0.3, 7.1±0.2, 6.8±0.3, 6.5±0.2 and 6.6±0.2, and correspondingly effluent pH increased to 8.0±0.2, 8.0±0.2, 8.2±0.2, 7.9±0.1 and 7.8±0.1 respectively, as shown in FIG. 5B. The high microbial biomass (25-54% of dry solids) and urea present in blackwater (Jang et al. 2015) may have contributed to the rise in pH.

$$RCHNH_2COOH + 2H_2O \rightarrow RCOOH + NH_3 + CO_2 + 2H_2 \quad \text{Equation 3}$$

$$NH_2(CO)NH_2 + 3H_2O \rightarrow 2NH_4^+ + HCO_3^- + OH^- \quad \text{Equation 4}$$

$$NH_3 + H_2O + CO_2 \rightarrow NH_4^+ + HCO_3^- \quad \text{Equation 5}$$

$$[H^+] = K_1 K_h P_{CO_2}/HCO_3^- \quad \text{Equation 6}$$

In Equation [6], K1 is ionic strength and Kh is 0.0246 moles/L-atm. PCO$_2$ is the partial pressure of carbon dioxide.

Compared to the effluent pH of mesophilic blackwater treatment reported previously, such as Cunha et al. (2018b) (pH=7.4) and De Graaff et al. (2010) (pH=7.4-7.6), the effluent pH of our study is higher (P<0.05); which may be attributed to the faster hydrolysis and lower CO$_2$ dissolution under higher temperature conditions. The increased pH in the thermophilic reactor may have contributed to the observed CaP formation. Cunha et al. (2018b) reported that CaP is only formed in the center of the granular sludge due to an observed pH increase (7.9) in the center of the granules caused by the consumption of hydrogen ion (H+) inside granules.

UASB Sludge VSS Concentrations, Specific Methanogenic Activities

Figures 6A, 6B:
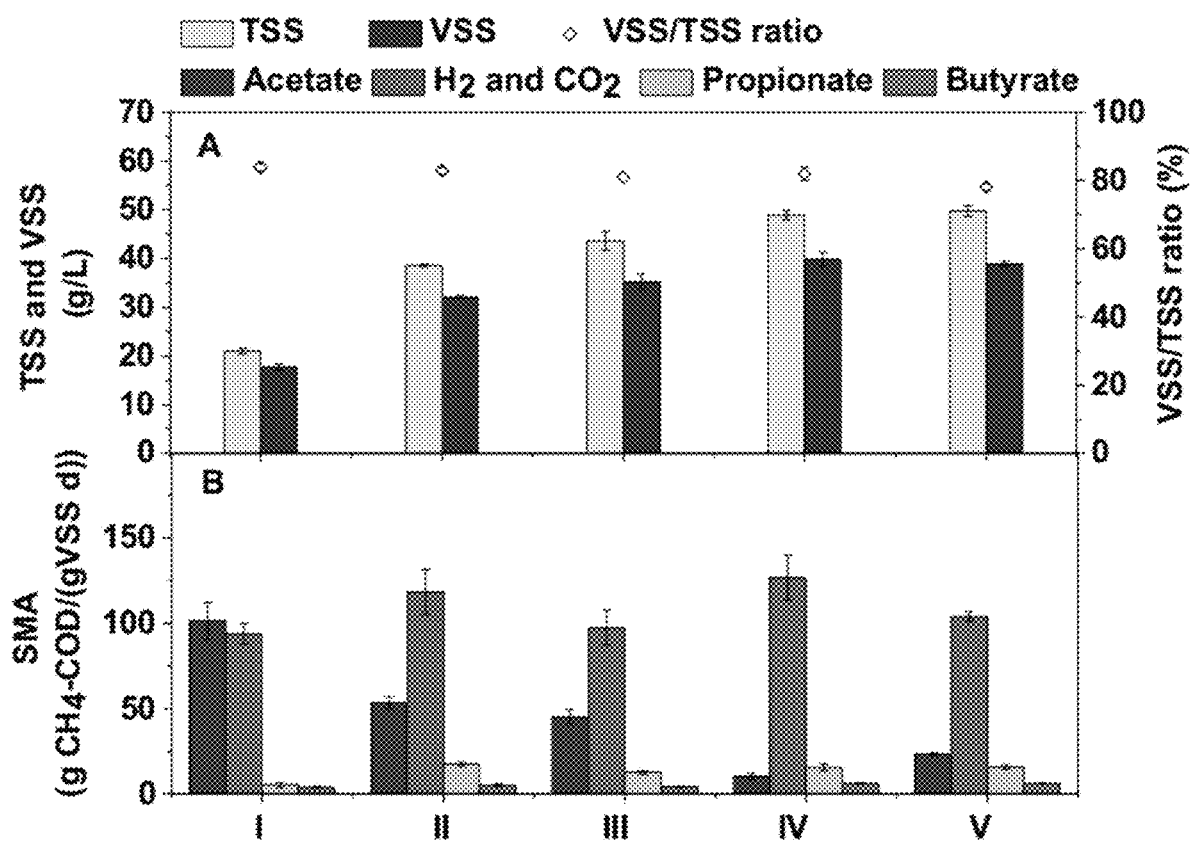
FIG. 6A is a graph showing concentrations of TSS and VSS, VSS/TSS ratio over the five reactor operation phases where error bars represent standard deviation of triplicate samples.
FIG. 6B is a graph showing concentrations of sludge SMA over the five reactor operation phases where error bars represent standard deviation of triplicate samples.

An important consideration in UASB reactor operation is loss of reactive biomass with build-up of inert solids. However, as shown in FIG. 6A, the VSS concentration of the sludge at the start-up phase significantly increased from 17.8±0.7 in Phase I to 32.1±0.2 g/L in the Phase II, then gradually increased to 38.9±0.6 g/L by Phase V. Importantly, the VSS/TSS ratio ranged from 78±1% to 84±1% as shown in FIG. 6A, which is in the range commonly reported for anaerobic sludge, indicating phosphorous precipitation did not significantly impact VSS/TSS ratio under the current experimental conditions.

Conswastent with a local pH upshift within solids is the predominance of hydrogenotrophic methanogenesis in solids from Phase II to V, as shown in FIG. 6B. The SMA of hydrogenotrophic methanogenesis varied from 93.9 mg CH$_4$—COD/(gVSS d) to 126.7 mg CH$_4$—COD/(gVSS d) over the four phases. The activity of acetoclastic methanogens clearly decreased from 101.3±10.8 mg CH$_4$—COD/(gVSS d) in the Phase I to 10.2±1.9 mg CH$_4$—COD/(gVSS d) in Phase IV. Further, as shown in FIG. 6B, the SMA of the sludge using propionate or butyrate as substrate is low and they ranged from 5.1±1.4 mg CH$_4$—COD/(gVSS d) to 17.3±1.2 mg CH$_4$—COD/(gVSS d) and from 3.910.7 mg CH$_4$—COD/(gVSS d) to 6.2±0.3 mg CH$_4$—COD/(gVSS d), respectively. It can be concluded that the fermentation in the thermophilic digestion produced mainly hydrogen, and therewith hydrogenotrophic methanogens are enriched (Zhang et al. 2020a). Overall, our SMA results suggest that methanogenic activity is not hindered by simultaneous phosphorus precipitation.

Sludge Characterization

Figure 7:
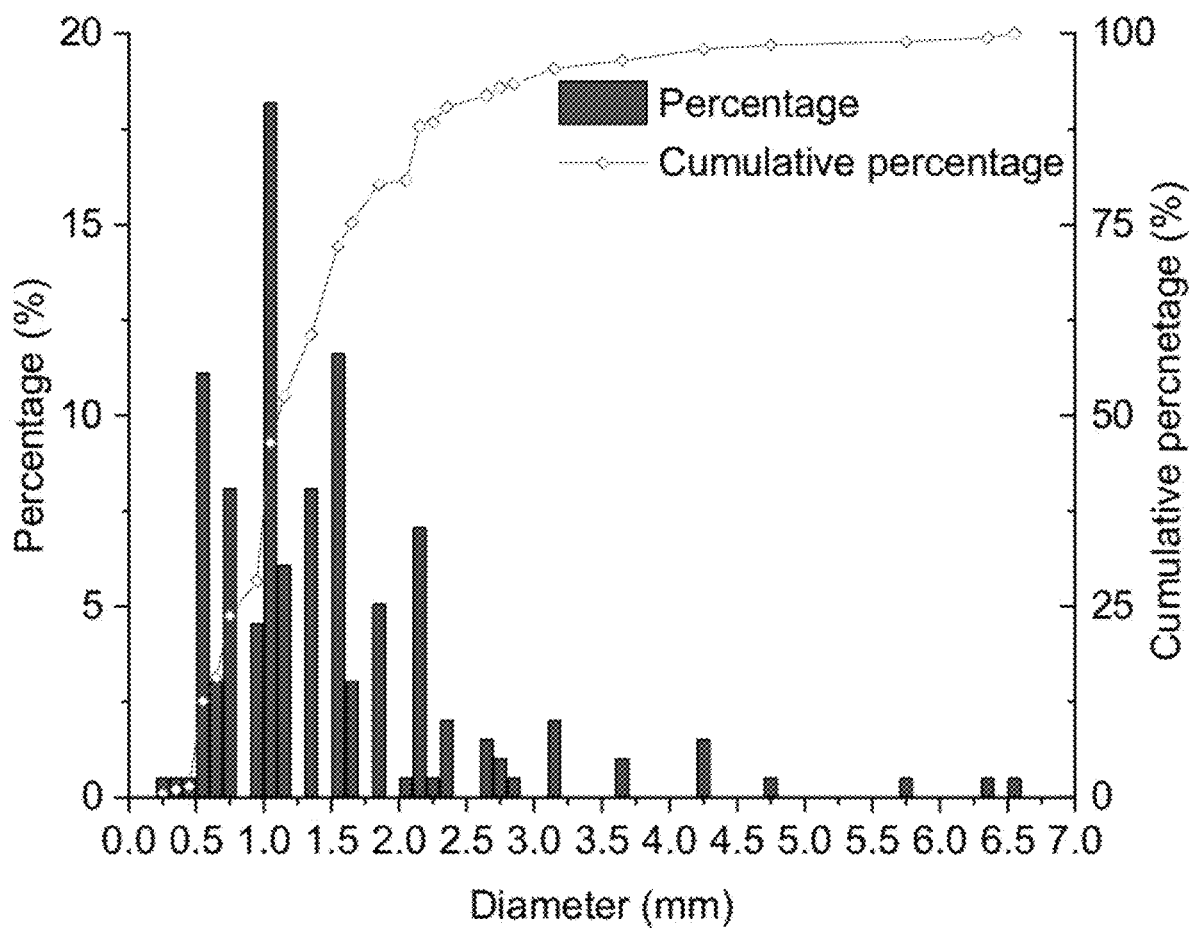
FIG. 7 is a graph showing granular sludge size distribution and cumulative percentage of the thermophilic sludge collected from Phase IV.

Granular sludge is observed in the thermophilic UASB reactor, as shown in FIG. 7, with dominant granule size (52.0%) ranging between 1 mm and 2 mm. The granular sludge size distribution is similar throughout Phases III to V, and as representative of these phases, only the results of sludge collected in Phase IV are presented here.

Figure 8A:
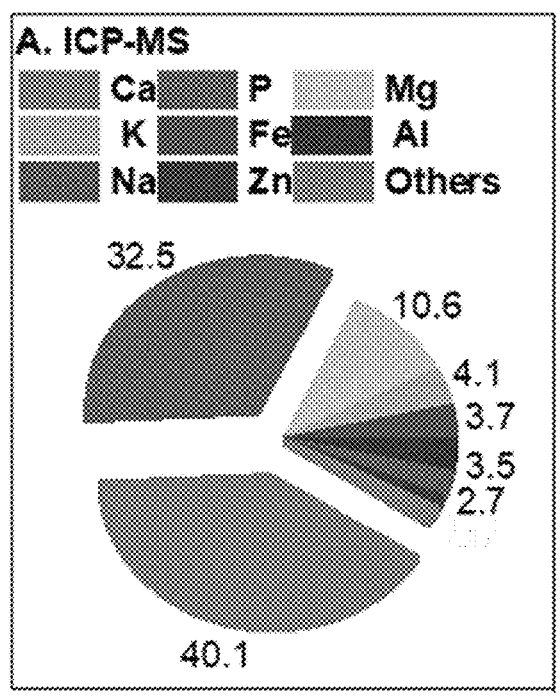
FIG. 8A is an exploded pie chart showing thermophilic UASB sludge collected from operation Phase IV, characterized by ICP-MS.

The predominant metal elements in Phase IV thermophilic UASB sludge are calcium (40.1%) and phosphorus (32.5%), with traces of magnesium (10.6%), potassium (4.1%), iron (3.7%), and aluminum 3.5%, as shown in FIG. 8A. The Ca:P molar ratio in the sludge is 1.0, conswastent with the Ca:P mole ratio (1.0±0.3) between influent and effluent described above (P>0.05).

Figure 8B:
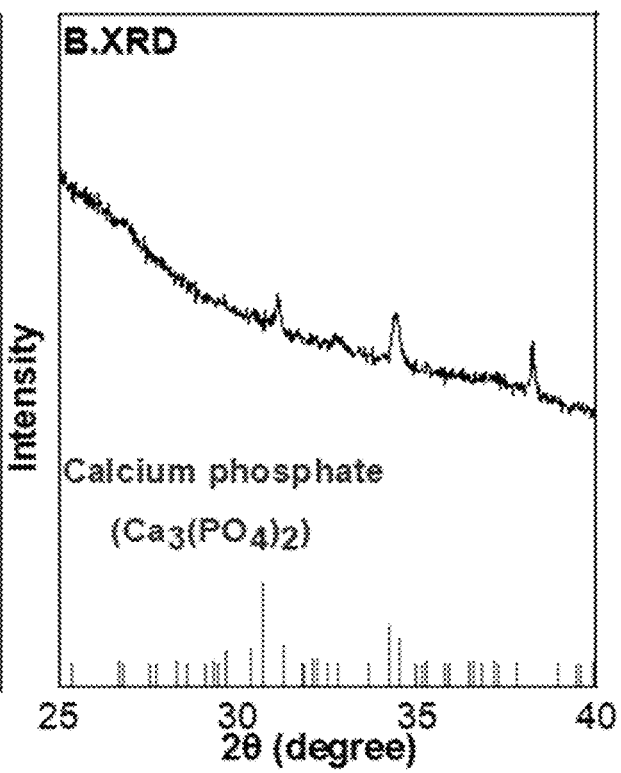
FIG. 8B is a graph showing thermophilic UASB sludge collected from operation Phase IV, characterized by XRD.
Figure 8C:
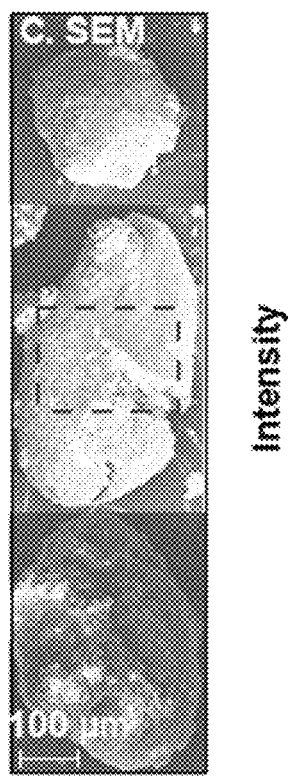
FIG. 8C is a microscopic image showing thermophilic UASB sludge collected from operation Phase IV, characterized by SEM.
Figure 8D:
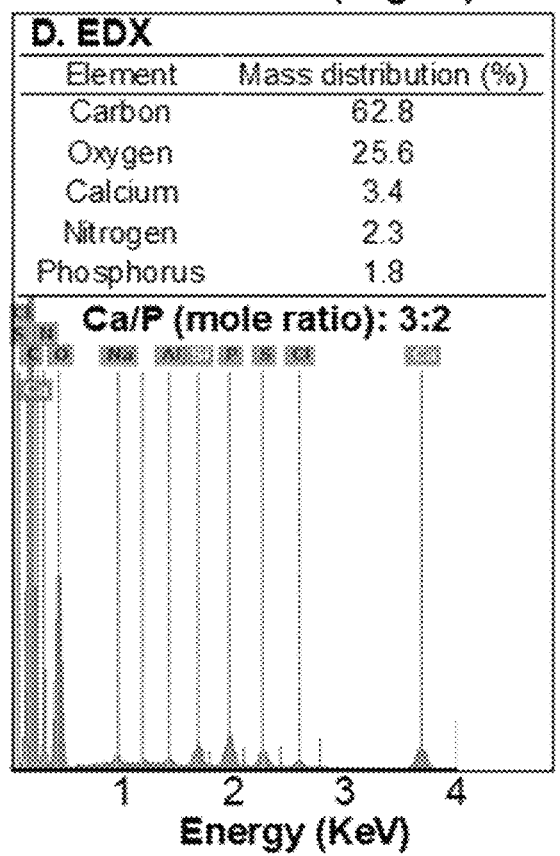
FIG. 8D is an energy versus intensity plot showing thermophilic UASB sludge collected from operation Phase IV, characterized by SEM-EDX.

To further explore the chemistry of Phase IV sludge, XRD analysis identified tricalcium phosphate (TCP, Ca3(PO4)2, Ca:P ratio of 1.5), as shown in FIG. 8B. SEM imaging showed spherical shaped granules formed in the reactor, as shown in FIG. 8C, and SEM-EDX analysis demonstrated that the Ca:P ratio is 3:2, in agreement with the XRD result, as shown in FIG. 8D. Nonetheless, mixed species of various crystalline forms of CaP are expected, as previously reported to dominant in anaerobic digesters: tricalcium phosphate (TCP, Ca$_3$(PO$_4$)$_2$, Ca:P ratio of 1.5) and the associated amorphous calcium phosphate (ACP, Ca$_3$(PO$_4$)$_2$.nH$_2$O, Ca:P ratio of 1.5) (Daneshgar et al. (2018)). For blackwater treatment sludge, Tervahauta et al. (2014) reported a mixture of hydroxyapatite (HAP, Ca$_{10}$(PO$_4$)6(OH)$_2$, Ca:P ratio of 1.67) and ACP are found during anaerobic digestion at 25° C. with Ca$^{2+}$ addition. The solubility constant (pKsp) of HAP (pKsp=58.6) is higher than that of ACP (pKs=25.5) and TCP (pKs=32.6), and therefore HAP is a more stable form of CaP precipitate (Daneshgar et al. 2018). It has been reported that pH plays an important role in CaP formation (Cunha et al. 2018b), and that HAP can only be formed under higher pH conditions (>pH 10) (Amjad 1998).

Figure 9:
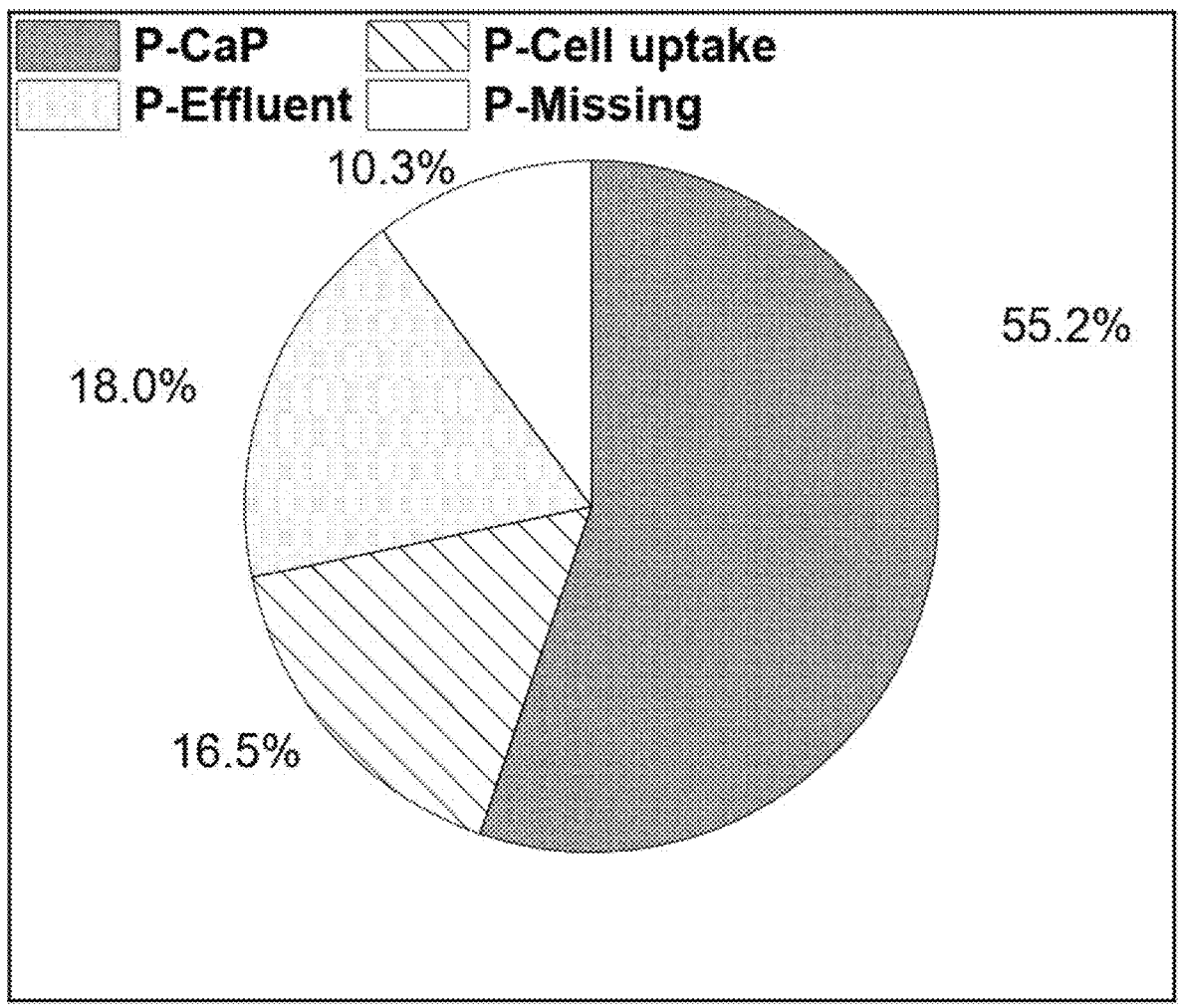
FIG. 9 is a pic chart showing phosphorous mass balance calculated based on ICP measurements. P—CaP represents the percentage of P precipitated as CaP in sludge, P-Cell uptake refers to the percentage of P incorporated into biomass, P-Effluent is the P amount in UASB reactor effluent, and $P_{Missing}$ represents the amount of P unaccounted for in the system.

It can be noted that, as compared to the molar ratio of the removed Ca: removed P from the reactor (Ca:P=1.0±0.3), and the Ca:P molar ratio observed using ICP-MS analysis (Ca:P=1), as discussed above, the obtained Ca:P ratios from XRD (Ca:P=1.5, based on main CaP species identified Ca$_3$(PO$_4$)$^2$) and SEM-EDX (Ca:P=1.5) are higher. This observation is related to the fact that XRD and SEM-EDX only examined the surface elemental composition of the granular sludge, excluding contribution from biomass phosphorus contents. As shown in FIG. 9, the removed phosphorus is largely attributed to CaP precipitation in the reactor (55.2%), with an additional 16.5% reduction through biomass P accumulation, estimated based on VSS contents and the assumption that phosphorus contributes to 2% of dry cell biomass. Hence, ICP-MS results can be used to calculate the Ca/P accumulated outside cells, which is 1.4, very close to XRD results.

Microbial Community Analysis

Bacterial Community

Figure 10A:
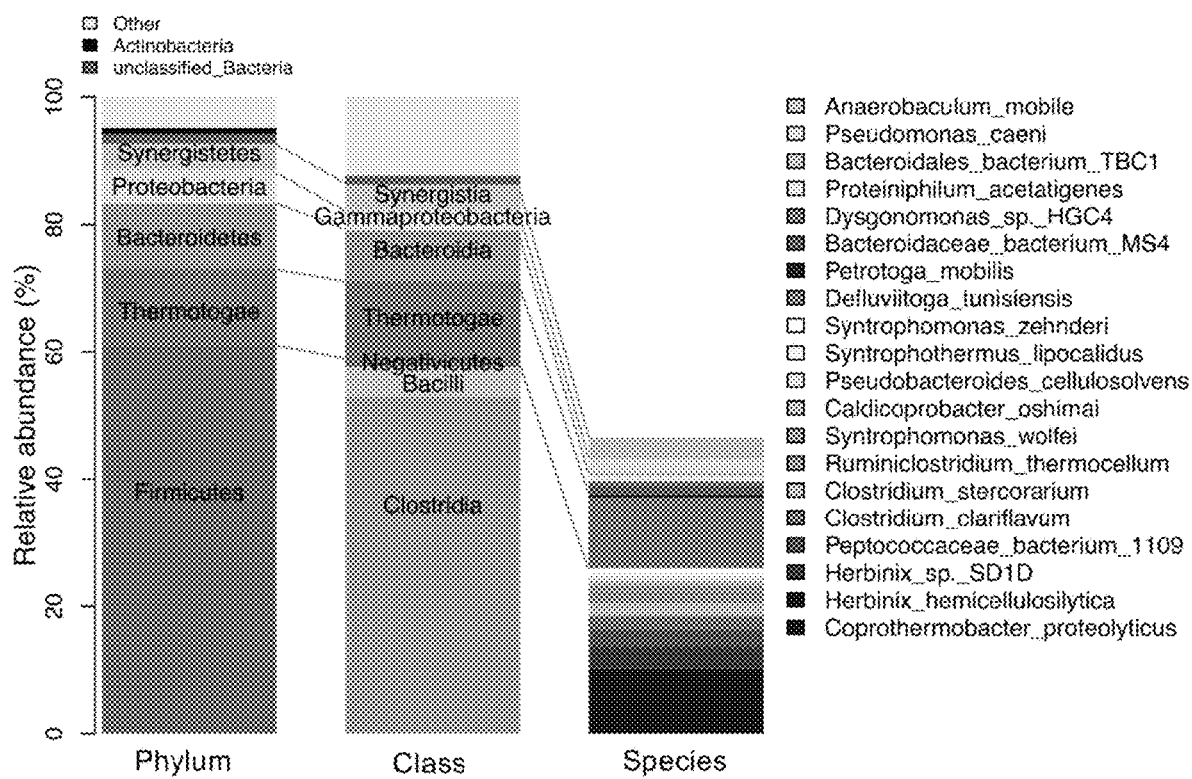
FIG. 10A shows relative abundances of bacteria at phylum, class, and species levels where "Other" indicates microbes with relative abundance below 1% and where the top 20 most abundant species are shown.

Within the bacterial community, as shown in FIG. 10A, Firmicutes (60.7%), Thermotogae (12.4%) and Bacteroidetes (10.2%) are the dominating phyla, followed by Proteobacteria (5.4%) and Synergwastetes (4.0%). Firmicutes and Bacteroidetes include most of the known hydrolytic bacterial species (Jing et al. 2017), indicating a strong hydrolysis functioning microbial community.

The metagenomics sequencing enabled high resolution of microbial community composition at species level. *Defluviitoga tunisiensis* is the most predominant species (11.1%), reported as a hydrolytic bacterium (Cibis et al. 2016; Maus et al. 2016). *Coprothermobacter proteolyticus* is the second abundant (6.2%), known for proteolytic activity (Gagliano et al. 2015; Kersters et al. 1994). Other abundant species with protein/peptide hydrolysis functions are *Anaerobaculum mobile* (3.3%) (Menes and Muxi 2002), *Proteiniphilum acetatigenes* (0.8%) (Chen and Dong 2005) and Peptococcaceae bacterium 1109 (2.6%) (Wirth et al. 2019), suggesting important protein/peptide hydrolysis activity. *Herbinix hemicellulosilytica* (4.0%) and *Herbinix* sp. SD1D (3.3%) have been reported to degrade cellulose (Koeck et al. 2015; Koeck et al. 2016). Several abundant species in the reactor are reported to hydrolyze cellulose, hemicellulose and lignocellulose, e.g. *Clostridium clariflavum* (2.3%) (Artzi et al. 2015), *Clostridium stercorarium* (2.0%) (Broeker et al. 2018; Poehlein et al. 2013), Ruminiclostridium thermocellum (2.0%) (Sheng et al. 2016), *Dysgonomonas* sp. HGC4 (0.9%) (Vera-Ponce de León et al. 2020), *Caldicoprobacter oshimai* (0.7%) (Yokoyama et al. 2010), and *Pseudobacteroides cellulosolvens* (0.7%) (Dassa et al. 2015).

Some species are syntrophic bacteria in partnership with methanogens, e.g. *Syntrophomonas wolfei* (0.9%) (Sieber et al. 2015), *Syntrophothermus lipocalidus* (0.7%) (Sekiguchi et al. 2000), and *Syntrophomonas zehnderi* (0.6%) (Sousa et al. 2007). These bacteria produce hydrogen and acetate, which are taken by methanogens. The well-established syntrophic relationship can explain the high methane production rate achieved in the current study.

Archaeal Community

Figure 10B:
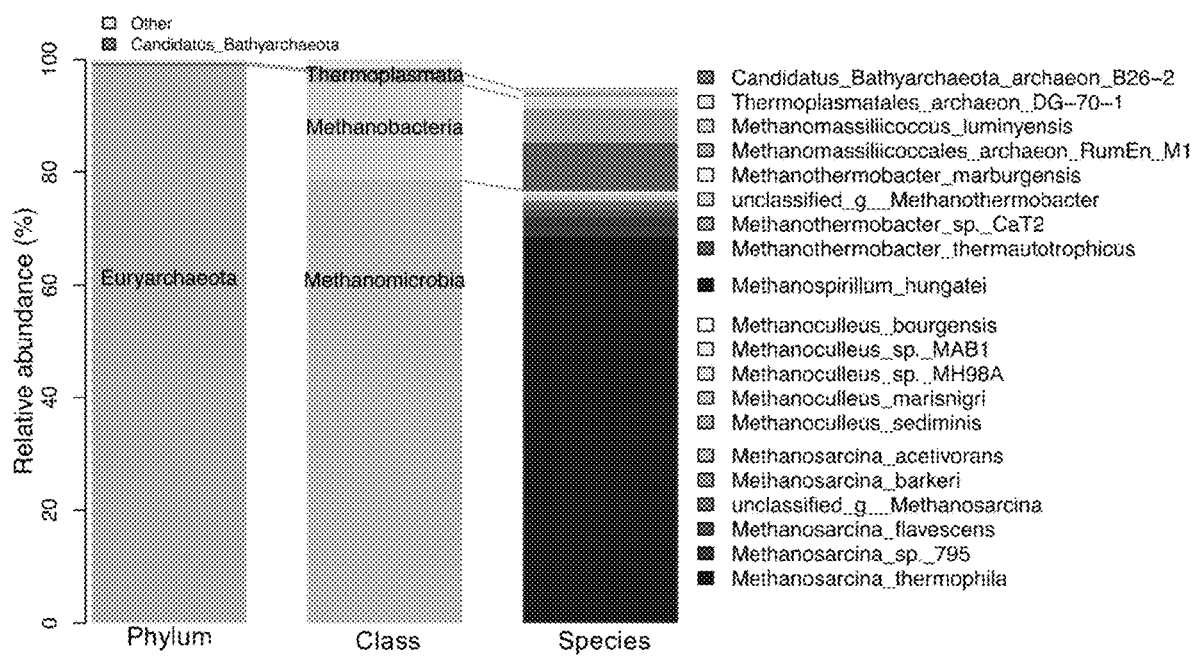
FIG. 10B shows relative abundances of archaea at phylum, class, and species levels where "Other" indicates microbes with relative abundance below 1% and where the top 20 most abundant species are shown.

The archaeal community, as shown in FIG. 10B, is dominated by the phylum Euryarchaeota (98.9%), composed of dominating classes Methanomicrobia (78.7%), Methanobacteria (17.2%) and Thermoplasmata (1.9%). The predominant methanogens at genus level are *Methanosarcina* (75.8%), *Methanothermobacter* (16.5%) and *Methanoculleus* (1.3%). *Methanosarcina* are versatile methanogens that utilize hydrogenotrophic, acetoclastic, and methylotrophic pathways to produce methane, and have been previously reported as the major genus in anaerobic digestion of blackwater (Gao et al. 2019a; Zhang et al. 2019). The identified *Methanosarcina* species are *Methanosarcina thermophila* (68.8%), *Methanosarcina* sp. 795 (3.3%), *Methanosarcina flavescens* (1.4%), *Methanosarcina barkeri* (0.2%), and *Methanosarcina acetivorans* (0.2%). *Methanothermobacter* and *Methanoculleus* are hydrogenotrophic methanogens observed in thermophilic AD (Cheng et al. 2011). The identified abundant *Methanothermobacter* species are *Methanothermobacter thermautotrophicus* (8.5%), *Methanothermobacter* sp. CaT2 (6.1%), and *Methanothermobacter marburgensis* (0.3%).

Functional Genes in Microbial Communities

In order to better interpret the key roles of microbes enriched in the reactor, the relative contribution of different species to the key functional genes are analyzed, i.e. urease (ureC, ureB, ureA, ureAB), alkaline phosphatase (phoA, phoB, phoD, phoB1, phoP), formyltetrahydrofolate synthetase (fhs, syntrophic acetate oxidation) in bacteria, and methyl-coenzyme M reductase (mcr) in archaea.

Figure 11:
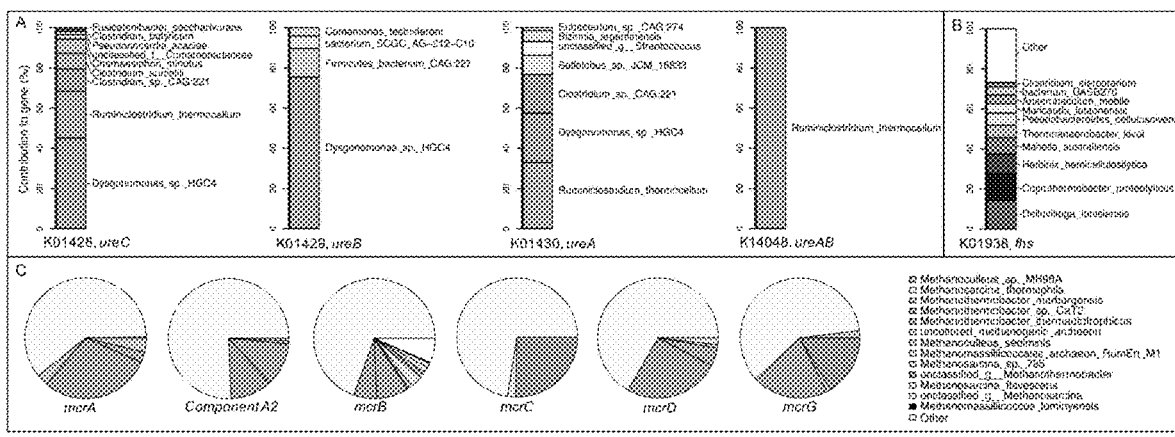
FIG. 11 shows relative contributions by microbial species to key functional genes encoding Urease (A), Formyltetrahydrofolatesynthetase (B), and Methyl-coenzyme M reductase (C) where the top 10 species contributing to each gene are shown.

The urease (EC 3.5.1.5) genes, as shown in FIG. 11A are contributed highly from *Dysgonomonas* sp. HGC4 and Ruminiclostridium thermocellum. *Dysgonomonas* sp. HGC4 contributed 45.2% of the urease subunit alpha (ureC, KEGG K01428) gene abundance, 75.5% of the urease subunit beta (ureB, K01429) and 24.7% urease subunit gamma (ureA, K01430). Ruminiclostridium thermocellum contributed 23.0% of the urease subunit alpha (ureC) gene abundance, 32.9% of the urease subunit gamma (ureC) and 100% urease subunit gamma/beta (ureAB, K14048). *Dysgonomonas* sp. HGC4 and Ruminiclostridium thermocellum are the thirteenth and tenth most abundant species in bacterial community, as shown in FIG. 10A, which play an essential role in urea hydrolysis leading to the increase of pH.

As a result of protein and urea hydrolysis, the total ammonia and free ammonia concentration increased (Equation [3] and [4]), which may induce a syntrophic acetate oxidation-hydrogenotrophic methanogenesis (SAO-HM) pathway (Westerholm et al. 2016). Formyltetrahydrofolate synthetase (fhs, K01938) has been identified as a functional marker for SAO (Müller et al. 2016), which is contributed by *Defluviitoga tunisiensis* (14.3%), *Coprothermobacter proteolyticus* (13.6%), *Herbinix hemicellulosilytica* (9.7%), *Mahella australiensis* (8.1%), *Thermoanaerobacter kivui* (6.2%) and *Pseudobacteroides cellulosolvens* (6.1%), as shown in 11B. These species are among the most abundant ones in the bacterial community, resistant to high free ammonia and showing functional SAO potentials. The archaeal partners for HM are reported to include the most abundant archaeal species in the current study, i.e. *Methanosarcina*, *Methanothermobacter* and *Methanoculleus* (Han et al. 2019; Mosbæk et al. 2016).

In all methanogenesis pathways, methyl coenzyme M reductase (mcr) catalyzes the last step of methanogenesis. As shown in FIG. 11C, *Methanosarcina thermophila* had the highest contributions to all mcr genes, mcrA (60.4%), component A2 (75.6%), mcrB (69.4%), mcrC (60.0%), mcrD (72.5%), and mcrG (66.8%). *Methanothermobacter thermautotrophicus*, *Methanothermobacter* sp. CaT2, and one unclassified species in *Methanothermobacter* also showed high contributions for mcr. The mcr gene contribution profiles are in accordance with the archaeal community composition, which is predominated by *Methanosarcina thermophila*, *Methanothermobacter thermautotrophicus*, and *Methanothermobacter* sp. CaT2.

DISCUSSION

High Treatment Performance and Granular Sludge Formation

In developing compact and efficient energy and nutrient recovery systems for wastewater resource recovery, UASB digestion is being revisited, particularly for higher strength streams such as blackwater (which may also contain food waste residuals for kitchen grinders) (De Graaff et al. 2010; Gao et al. 2020b). A key finding during our present study is that thermophilic UASB treatment of blackwater is far superior to reports from previous studies of anaerobic digestion of blackwaters (Gao et al. 2019b; Moges et al. 2018; Wendland et al. 2007).

Figure 12:
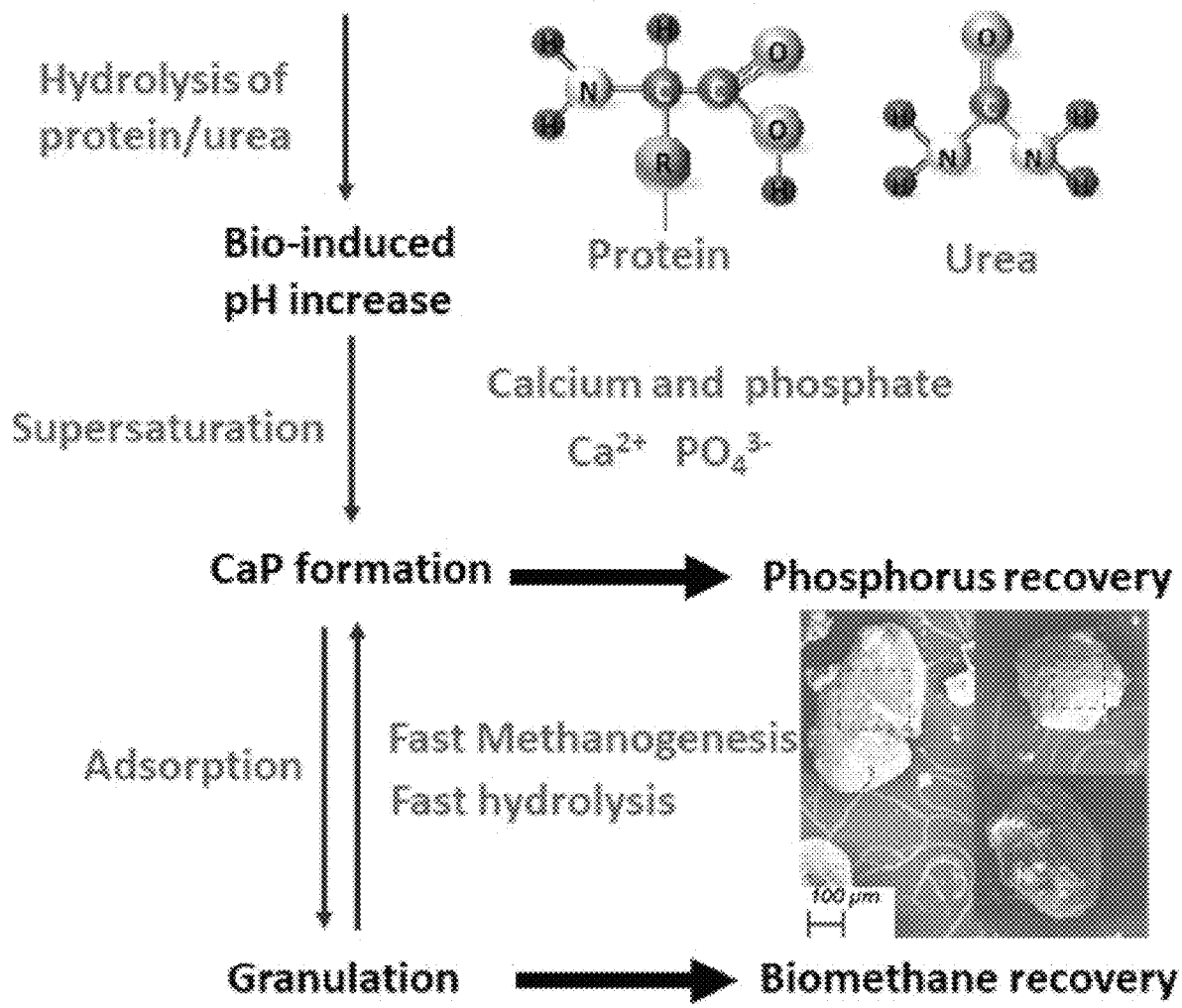
FIG. 12 is a schematic diagram of simultaneous phosphorus recovery in energy generation reactor (SPRING) treating blackwater.

We achieved a high methane yield (2.4±0.1 NL $CH_4$/(L d)), a short HRT (2.5 days) and the highest OLR reported for blackwater treatment (up to 12.4 kg COD/($m^3$d)) by thermophilic UASB treatment. Despite the fluctuation of feed blackwater quality changes studied, the treatment is stable throughout the 190 days of operation, with minimal VFA or inert solids accumulation observed. The high OLR achieved in the present study can be attributed to the following three reasons, as described in FIG. 12.

Firstly, thermophilic UASB treatment efficiently improves hydrolysis of blackwater solids, which has been demonstrated as the rate limiting step during blackwater anaerobic digestion (Gao et al. 2019b). The blackwater solids contain undigested food residues like fiber, undigested protein and lipid, which can result in slow hydrolysis (Rose et al. 2015). The successful operation of the present study is at least partially attributed to high hydrolysis rate constant in thermophilic reactor. The batch experiments showed that the hydrolysis rate constant (kh) in thermophilic condition reached 0.3-1 (Zhang et al. 2020b), as compared to the kh ranging from 0.1 to 0.2-1 (Cheng et al. 2018; Elmitwalli and Otterpohl 2007), reported in previous blackwater studies. Similar improvement in hydrolase activity and solubility of solids content under elevated temperature conditions has been reported previously, treating various feedstock types (De La Rubia et al. 2013; Speece 2008).

Secondly, the high methanogenic activity under thermophilic treatment conditions further improved treatment efficiency and prevented VFA accumulation. As compared to the methane production rate of a UASB blackwater reactor (0.02 NL CH/(gVSS d)) under mesophilic conditions (Gao et al., 2019), our thermophilic methane production rate reached 0.06 NL CH/(gVSS d). The methane production rate of the sludge and the performance of the thermophilic reactor indicated that no free ammonia inhibition took place in the current study, although free ammonia concentration is high (421 mg-N/L) under the thermophilic condition. The stability of methanogenesis could be attributed to the predominance of hydrogenotrophic methanogens, known to be more resistant towards free ammonia inhibition, as compared to acetoclastic methanogens (Gao et al. 2019a). In particular, the dominance of *Methanosarcina* could have contributed to the high methanogenic activities, largely due to its multi substrate utilization capacity, high substrate utilization rate and morphology feature of cell aggregates (Cheng et al. 2018; Florentino et al. 2019).

Lastly, the fine granules formed in our UASB reactor may have contributed to the high OLR achieved in this study, through retaining a high biomass concentration with VSS concentration of 38.9±0.6 g/L in the thermophilic reactor. In comparison, previous studies on UASB treatment of blackwater reported VSS concentrations ranged from 19-28 g/L (De Graaff et al. 2010; Gao et al. 2019b). Similar VSS concentration (45-52 g/L) is achieved by (Yoochatchaval et al. 2008) using an expended granular sludge reactor (EGSB) for low strength wastewater treatment. A better settling property of the granular sludge can contribute to long sludge retention time and high biomass concentration in anaerobic reactors, like UASB reactor and internal circulation (IC) reactor (Fukuzaki et al. 1995). However, considering the improvement of methane yield in the present study (3.6 folds as compared to Gao et al. (2019b)), the increased VSS (1.5-2 folds increase) only contributed partially to the performance. Three mechanism presented in this section most likely are all playing a role in improving the observed UASB treatment capacity.

High P Recovery and Formation of Granular Sludge

This is apparently the first study to focus on simultaneous P removal during anaerobic treatment without chemical addition, and produced a conswastent 77.7±8.5% removal of $PO_4^{3-}$—P. While phosphorus precipitation is dependent on multiple factors, key aspects likely include: small UASB reactor granules formed, localized high pH stimulated by hydrogenotrophic methanogens and a calcium content in the blackwater above 150 mg/L. As a result, Ca and P would be expected to precipitate (SI=1.43). In comparison, blackwater collected from conventional flushed toilets contains lower phosphorus concentration (about 10 times diluted compared to our simulated vacuum-flushed blackwater (Gao et al. 2020a)), which may help to explain our observed CaP precipitation.

Similar to the reported studies with Ca addition, reaching supersaturation values is one of the most important factors for CaP precipitation (Cunha et al. 2018a). However, previous work has demonstrated that even when supersaturation levels are reached, CaP precipitation may not occur in the anaerobic digester (De Graaff et al. 2010). For example, phosphorus removal is not observed by anaerobic reactors treating blackwater with similar Ca and P concentrations to those in the current study (Chen et al. 2016; Gao et al. 2019b; Zhang et al. 2019). Hence, reaching supersaturation levels alone cannot guarantee CaP precipitation.

Another key factor for Ca—P precipitation is likely to be high (localized) pH (ranging from 7.9-8.0), favored by rapid blackwater protein and urea hydrolysis under thermophilic conditions. A pH increase from 6.8 to 8.0 led to an increase in SI from −1.34 to 1.43 under current reactor operation conditions. Further, without methanogenesis keeping pace with hydrolysis, the observed phosphorus precipitation would not occur because of VFA accumulation and pH reduction.

Overall, it can be concluded that the high protein and urea contents of blackwater, together with the enhanced hydrolysis and methanogenesis rates observed through thermophilic UASB digestion, provide a new way to simplify phosphorus recovery from blackwater. We propose the following sequence starting with calcium-based precipitation assisting by forming the core of granular sludge, neutralizing the surface charge of microbial aggregates, and facilitating cell-cell bridging in granular sludge, as discussed in previous studies (Faria et al. 2019; Teo et al. 2000). The formation of granular sludge also improves the biomass density of the UASB sludge, promoting hydrolysis and methanogenesis rates, which led to the bio-induced pH increase in the bioreactor, further facilitating the precipitation and adsorption of CaP; leading to high P recovery within the reactor.

Engineering Implications

The observed simultaneous phosphorous and energy recovery from UASB treating blackwater (i.e., the SPRING process), is facilitated by the thermophilic conditions adopted for blackwater treatment. At a household or a small community scale, the temperature of collected blackwater from households is close to room temperature. While heating energy is required for the thermophilic UASB treatment of blackwater, compared to the highest treatment efficiency previously reported (0.68 m3 methane per $m^3$ per day)(Gao et al. 2019b), more than 3.5-fold methane is produced in the current study (2.44 $m^3$ methane per $m^3$ per day). In total, the energy produced through biomethane production is 258 $MJ/m^3$ treated blackwater. This value is greater than the energy required for reactor heating (126 $MJ/m^3$ blackwater treated). Additional benefits come from the phosphorus precipitation in UASB sludge, and significantly improved blackwater treatment efficiency.

CONCLUSIONS

Using a thermophilic UASB reactor to treat concentrated blackwater, we identified co-benefits through high biomethane production and phosphorus precipitation. Some 77.5±4.4% to 83.6±2.1% COD is removed at an OLR of 0.9-12.4 kg COD/($m^3$d) and methane yield of 55.9±6.2% to 60.8±1.8%. The blackwater P-removal is 77.7±8.5% during the entire operation period of 190 days. The key component of the granular sludge developed conswasted of Ca2+ (40.1%) and phosphorus (32.5%) with negligible heavy metal contamination. The Ca:P mole ratio in the sludge is close to 1.0, and the major species of calciumphosphate appeared to be tricalcium phosphate (TCP). Hence, the phosphorus recovered via reactor sludge can be used as fertilizer or as raw material by the phosphorus refinery industry. The produced biomethane could be used locally, noting that some 126 MJ/m³ blackwater would be required to heat the thermophilic UASB reactor.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A process for treating wastewater comprising:
inputting a stream of blackwater into a blackwater reactor;
treating the blackwater in the blackwater reactor with an anaerobic digestion process and with methanogenesis and hydrolysis treatment, independent of mixing;
controlling a pH level of the blackwater within the blackwater reactor;
recovering phosphorus precipitates from the blackwater reactor, optionally independent of chemical additives;
recovering methane from the blackwater reactor;
inputting a stream of treated blackwater into a greywater reactor and inputting a stream of greywater into the greywater reactor as contents of the greywater reactor; and
treating the treated the contents of the greywater reactor with a greywater treatment.

2. The process of claim 1, wherein the blackwater input stream contains at least 150 mg/L calcium.

3. The process of claim 1, wherein the pH level of the blackwater within the blackwater reactor is controlled to a pH of at least 7.5.

4. The process of claim 1, wherein the recovered methane is recovered at a rate of 2.44 m³ per m³ treated blackwater.

5. The process of claim 1, wherein the phosphorus precipitates recovered from the blackwater reactor comprise $PO_4^3$—with a concentration of at least 20 mg/L of treated blackwater.

6. The process of claim 1, wherein treating the blackwater further includes applying a thermophilic condition that includes a temperature of 52° C.

7. The process of claim 1, wherein the greywater treatment results in at least a 99% reduction of surfactant from the greywater.

8. The process of claim 1, further comprising eliminating free ammonia inhibition during the anaerobic digestion process and enhancing rates of the methanogenesis treatment during the anaerobic digestion process.

9. The process of claim 1, further comprising maintaining an operating temperature of the blackwater reactor of 35 to 55° C.

10. The process of claim 1, further comprising maintaining a COD/Alkalinity ratio in the blackwater reactor in the range of 1.5-3.

11. The process of claim 1, further comprising maintaining a phosphorus concentration in the blackwater reactor of at least 50 mg/L.

* * * * *